United States Patent
Wengreen et al.

(10) Patent No.: US 8,055,356 B2
(45) Date of Patent: Nov. 8, 2011

(54) LEAD SYSTEM HAVING FRICTION MECHANISM AND METHOD THEREFOR

(75) Inventors: Eric John Wengreen, Blaine, MN (US); Eric Falbe Hammill, Ham Lake, MN (US); Luke Thomas Babler, Shoreview, MN (US); Neil Becker, Fallbrook, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 663 days.

(21) Appl. No.: 11/427,167

(22) Filed: Jun. 28, 2006

(65) Prior Publication Data
US 2008/0004682 A1    Jan. 3, 2008

(51) Int. Cl.
*A61N 1/00* (2006.01)
(52) U.S. Cl. .................................... 607/126

(58) Field of Classification Search ............ 607/126, 607/127, 115, 116, 119, 120, 122, 125, 129, 607/132, 131; 600/585
See application file for complete search history.

(56) References Cited

U.S. PATENT DOCUMENTS

| | | | | |
|---|---|---|---|---|
| 4,106,512 A * | 8/1978 | Bisping | ......................... | 607/127 |
| 4,649,938 A * | 3/1987 | McArthur | ..................... | 607/127 |
| 5,514,173 A * | 5/1996 | Rebell et al. | ................... | 607/127 |
| 5,716,390 A * | 2/1998 | Li | .................................. | 607/127 |
| 6,585,655 B2 | 7/2003 | Crowley | | |
| 6,687,550 B1 * | 2/2004 | Doan | ............................. | 607/127 |
| 2003/0167082 A1 * | 9/2003 | Ollivier et al. | ................. | 607/126 |

* cited by examiner

*Primary Examiner* — George Manuel
*Assistant Examiner* — Robert Wieland
(74) *Attorney, Agent, or Firm* — Faegre & Benson LLP

(57) ABSTRACT

A lead system has an elongate body, an active fixation assembly movable relative to the elongate lead body, and a low variation friction member frictionally engaged with the active fixation assembly. In an option, the active fixation assembly undergoes greater torsional resistance as the active fixation assembly is moved in a direction to retract the lead.

21 Claims, 12 Drawing Sheets

LEAD SYSTEM HAVING FRICTION MECHANISM AND METHOD THEREFOR

TECHNICAL FIELD

Leads for conducting electrical signals to and from the heart, and more particularly, leads having a friction mechanism.

TECHNICAL BACKGROUND

Pacemaker leads represent the electrical link between the pulse generator and the heart tissue, which is to be excited and/or sensed. These pacemaker leads include single or multiconductors that are connected to an electrode in an electrode assembly at an intermediate portion or distal end of a pacing lead. A connector is included at the proximal end to form the electrical connection with the pacemaker.

To implant the lead within the patient, the lead is often fed intravenously toward the heart. The lead may be implanted within or travel through complex or tortuous vasculature. Once positioned at a desirable location, the lead is fixated to the patient at a location, for example, by actively fixating the lead to the heart. To actively fixate a lead, an element, such as a helical tip at the distal end of the lead, is rotated out of the lead and in to the patient. As the patient walks or moves about, and as the heart beats, the lead undergoes a series of forces. However, it is important that the lead does not become dislodged from the patient once the lead is fixated in place.

Accordingly, there is a need for a lead that resists dislodgement after the lead has been fixated to the patient.

SUMMARY

A lead system has an elongate body, an active fixation assembly movable relative to the elongate lead body, and a friction member frictionally engaged with the active fixation assembly. In an option, the active fixation assembly undergoes greater torsional resistance as the active fixation assembly is moved toward a retracted position.

A method is further provided which includes moving an active fixation assembly of an implantable lead system relative to an elongate, flexible lead body, where the elongate, flexible lead body extends from a proximal portion to a distal portion and the active fixation assembly is within the elongate flexible lead body. The lead system is optionally coupled with an energy source, such as, but not limited to, a pulse generator. The active fixation assembly is moved longitudinally, for example by rotation, to implant the active fixation member in tissue.

The method further includes providing a friction force, such as a linear friction force to the movable active fixation assembly as it is moved relative to the elongate, flexible lead body. An example of providing the linear friction force is placing a canted coil against an outer periphery of the active fixation assembly as the active fixation assembly is moved. When applying the force, in an option, the method includes placing a first torsional resistance against the active fixation assembly as the active fixation assembly is moved toward an extended position and placing a second torsional resistance against the active fixation assembly during retraction. For instance, the second torsional resistance is greater than the first torsional resistance.

These and other embodiments, aspects, advantages, and features will be set forth in part in the description which follows, and in part will become apparent to those skilled in the art by reference to the following description and referenced drawings or by practice thereof. The aspects, advantages, and features are realized and attained by means of the instrumentalities, procedures, and combinations particularly pointed out in the appended claims and their equivalents.

DESCRIPTION OF THE EMBODIMENTS

In the following detailed description, reference is made to the accompanying drawings, which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the spirit and scope of the present invention. Therefore, the following detailed description is not to be taken in a limiting sense, and the scope is defined by the appended claims.

Figure 1:
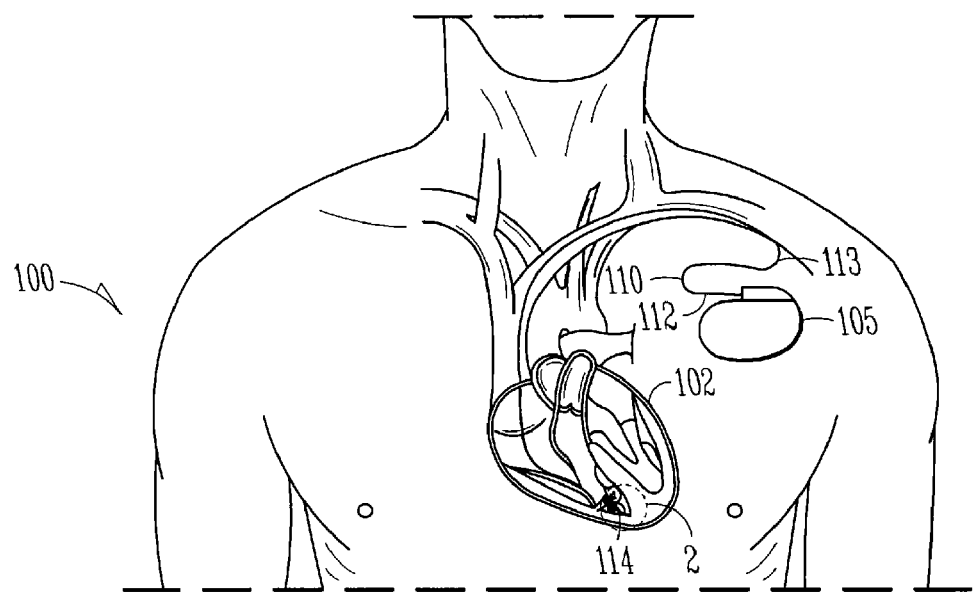
FIG. 1 illustrates a lead system constructed in accordance with at least one embodiment.

An extendable and retractable lead 110 and lead system 100 are illustrated in FIG. 1, that shows a system for delivering and/or receiving electrical pulses or signals to stimulate and/or sense tissue, such as the heart 102. The system 100 includes a pulse generator 105 and a lead 110. The pulse generator 105 includes a source of energy as well as an electronic circuitry portion. The pulse generator 105, in one option, is a battery-powered device that generates a series of timed electrical discharges or pulses. The pulse generator 105 is generally implanted into a subcutaneous pocket made in the wall of the chest. Alternatively, the pulse generator 105 is placed in other places within or near a body, for example, within a subcutaneous pocket made in the abdomen, or in other locations.

Figure 2:
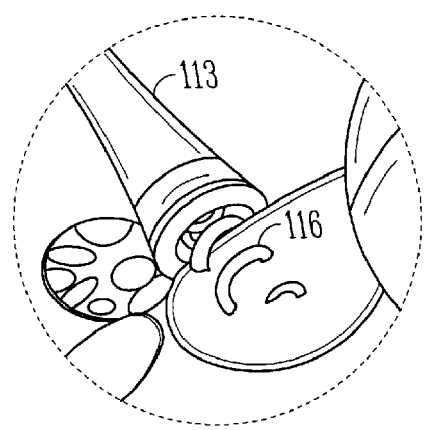
FIG. 2 illustrates a portion of a lead system implanted within tissue constructed in accordance with at least one embodiment.

The lead 110 includes a lead body 113 that extends from a proximal end portion 112, where it is coupled with the pulse generator 105, to a distal end portion 114. The lead 110 further includes at least one electrode 116 (FIG. 2) which electrically couples the lead 110 with tissue, such as the heart 102. At least one electrical conductor 118 (FIG. 3A) is disposed within the lead 110 and extends, in one option, from the proximal end portion 112 to the distal end portion 114 of the lead 110. At least one electrical conductor 118 (FIG. 3A) electrically couples the electrode 116 with the proximal end portion 112 of the lead 110. The electrical conductors carry electrical current and pulses between the pulse generator 105 and the electrode 116 (FIG. 2). FIG. 2 illustrates the helix implanted within tissue, referred to as an extended position. When the helix is rotated, it can be removed from tissue, referred herein as a retracted position. It should be noted that the retracted position does not necessarily require the helix to be retracted within the lead body.

Figure 3A:
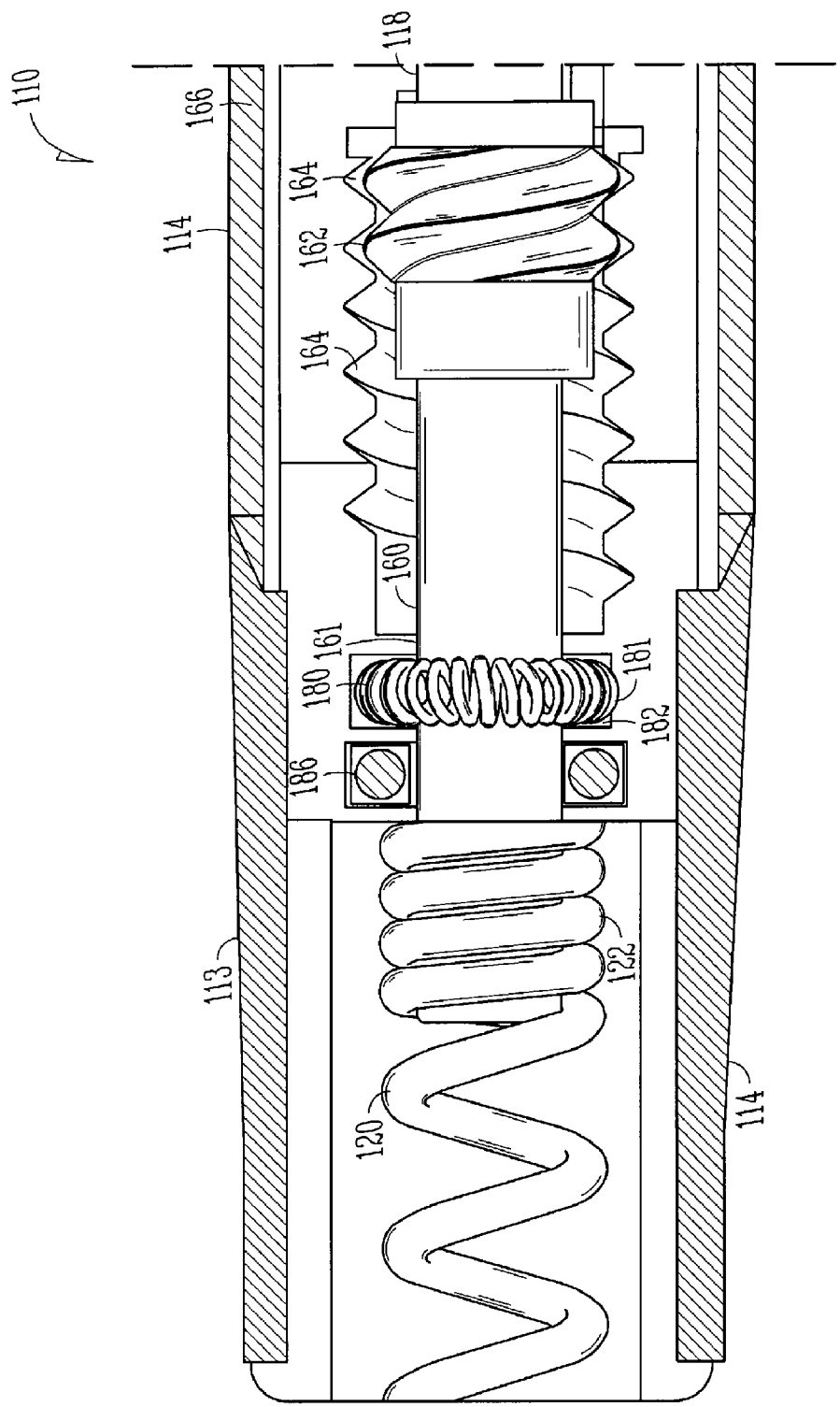
FIG. 3A is a cross-sectional view of a portion of a lead in a retracted position, constructed in accordance with at least one embodiment.
Figure 3B:
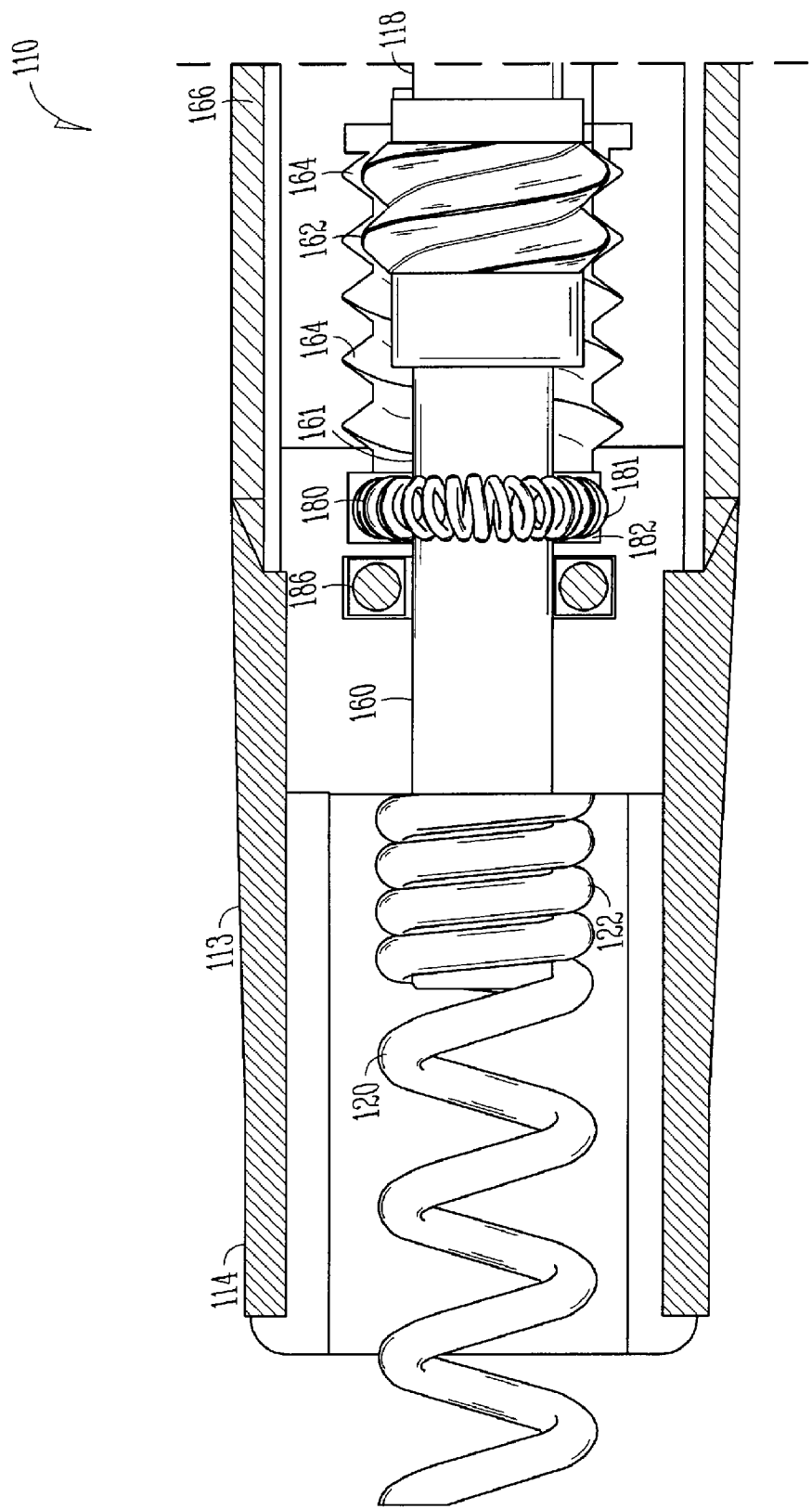
FIG. 3B is a cross-sectional view of a portion of a lead in an extended position, constructed in accordance with at least one embodiment.

FIGS. 3A, 3B, 9, and 10 illustrate examples for the distal end portion 114 of the lead 110 in greater detail, where FIG. 3A illustrates an example of the lead 110 in a retracted position and FIG. 3B illustrates the lead 110 in an extended position. The distal end portion 114 includes an active fixation assembly 122 that moves relative to the lead body, where the fixation assembly includes an active fixation member, such as a fixation helix 120. While a fixation helix is illustrated, other active fixation members can be included as well, such as, but not limited to barbs, or sharpened members.

Figure 9:
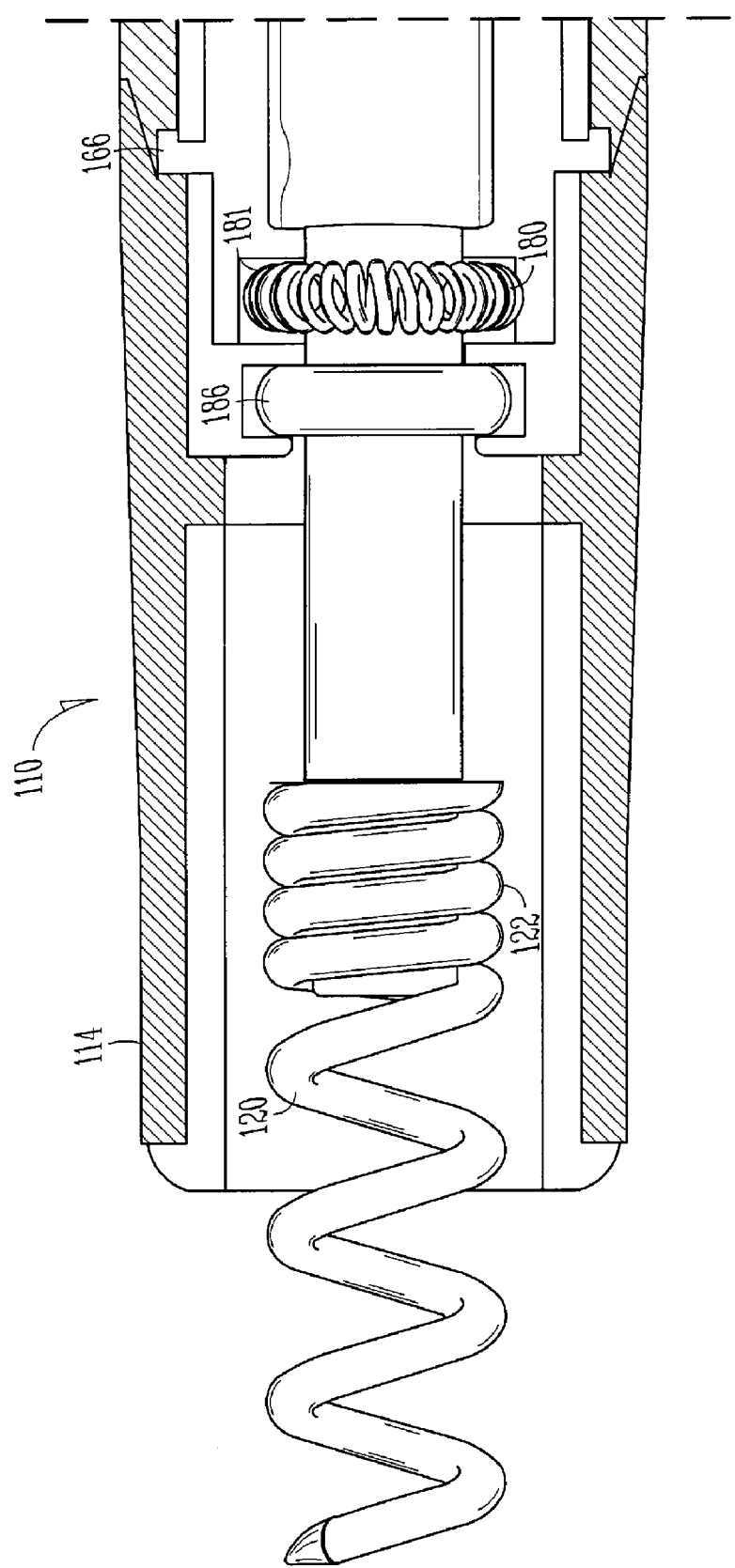
FIG. 9 is a cross-sectional view of a portion of a lead in a constructed in accordance with at least one embodiment.
Figure 10:
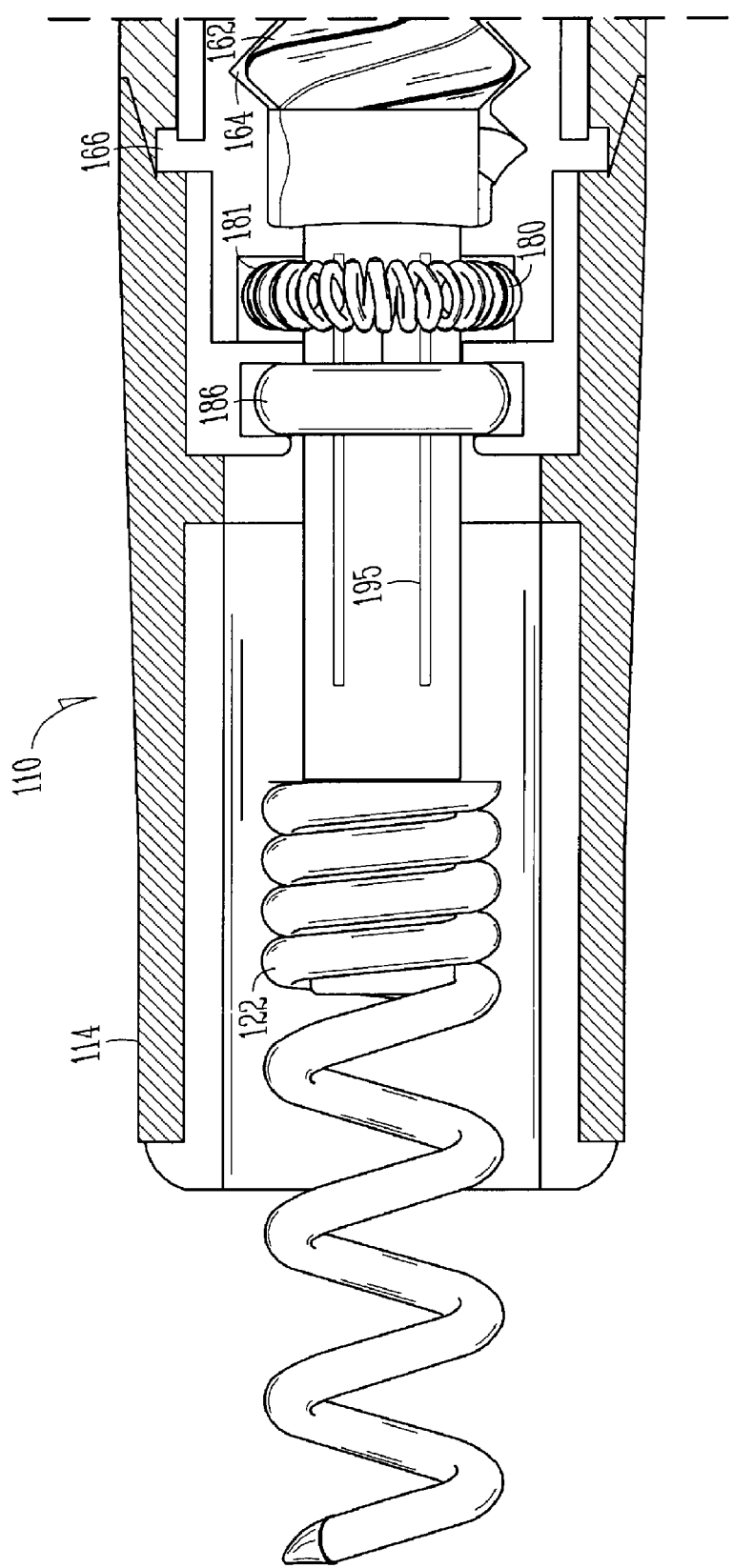
FIG. 10 is a cross-sectional view of a portion of a lead in a constructed in accordance with at least one embodiment.

The active fixation assembly 122 further includes an electrode base 160, which a serves as a piston. The piston, in an option, is electrically conductive, and is electrically coupled with the fixation helix 120. The piston is further mechanically coupled with the fixation helix 120, and allows for the fixation helix 120 to be advanced longitudinally through the lead body 113. With movement of the piston, the fixation helix 120 can be rotated, and optionally moved longitudinally, from a retracted position, as shown in FIG. 3A, to an advanced position, as shown in FIGS. 3B, 9, and 10. In another example, FIG. 9 illustrates a piston that is rotatable to rotate the fixation helix 120 to an advanced position without longitudinally moving the active fixation assembly. When placed in the advanced position, the lead 110 can be fixated with tissue, for example as illustrated in FIG. 2. The fixation helix 120 can also be moved longitudinally from the advanced position to the retracted position as the piston is moved longitudinally.

The piston optionally includes features that allow it to be moved longitudinally. For example, the piston includes a threaded portion 162 that engages with an internally threaded portion 164 of the piston housing 166, as shown in FIGS. 3A, 3B, and 10. To move the piston in longitudinal movement, the piston is rotated and the threaded portions engage each other to advance the piston and the fixation helix. In an option, the piston is controlled at the proximal portion of the lead 110 (FIG. 1), for example by turning the pin.

Figure 4:
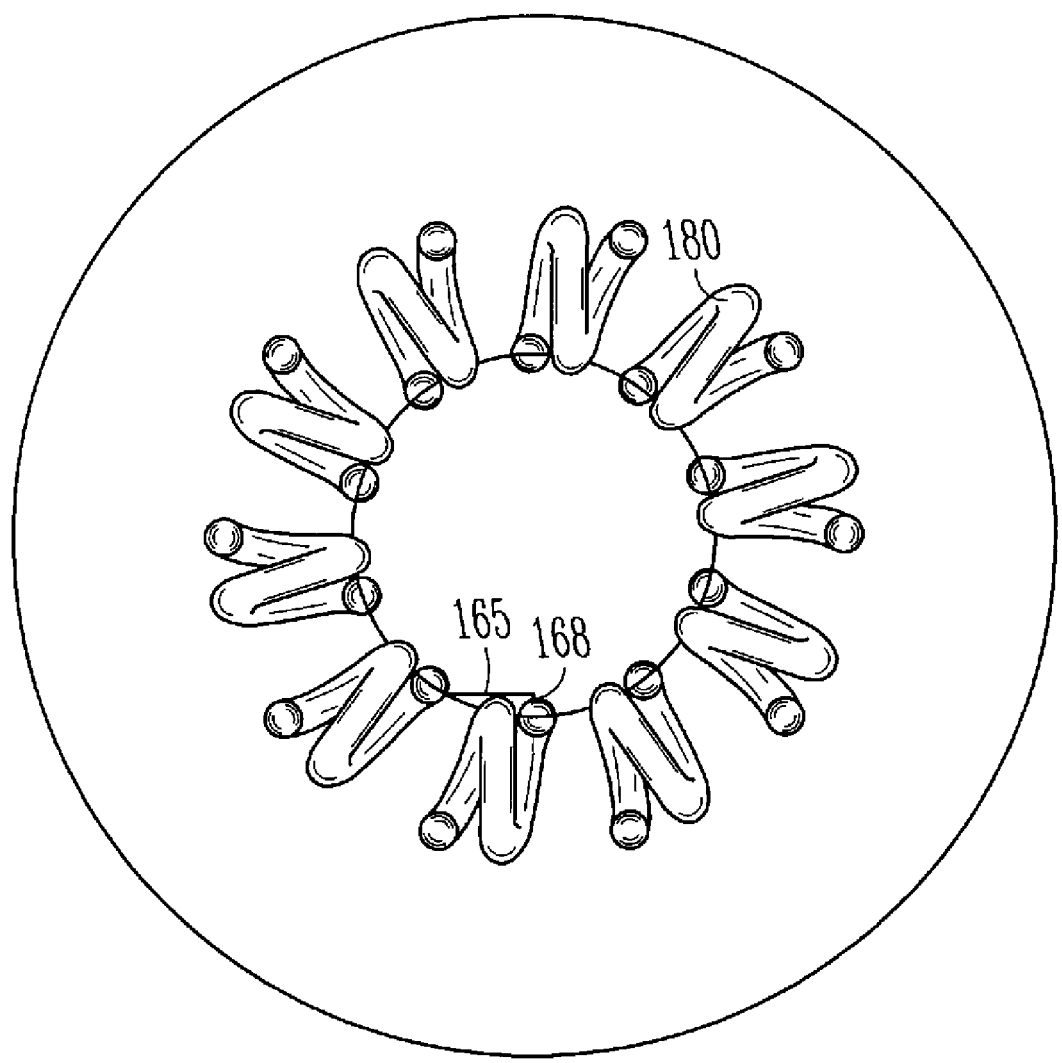
FIG. 4 is a cross-sectional view of a portion of a lead in accordance with at least one embodiment.

The piston frictionally interacts with a friction member 180 that is included with the lead 110, for example at a distal tip of the lead body 113 (FIG. 1). The friction member 180, in an option, is frictionally associated with the piston or the electrode base 160, as shown in FIGS. 3A, 3B, and 4. For example, the friction member 180 has an inner portion that at least partially surrounds an outer periphery 161 of the piston or electrode base, and optionally is in direct contact with the piston or the electrode base. The friction member 180, in an option, is frictionally associated with the piston housing 166, as shown in FIGS. 7A-10. For example, the friction member 180 has an outer portion that is in direct contact with the piston housing 166. In another option, a seal 186 is sealingly engaged with the outer periphery 161 of the piston or electrode base, which assists in preventing fluids from entering the lead 110.

Figure 5:
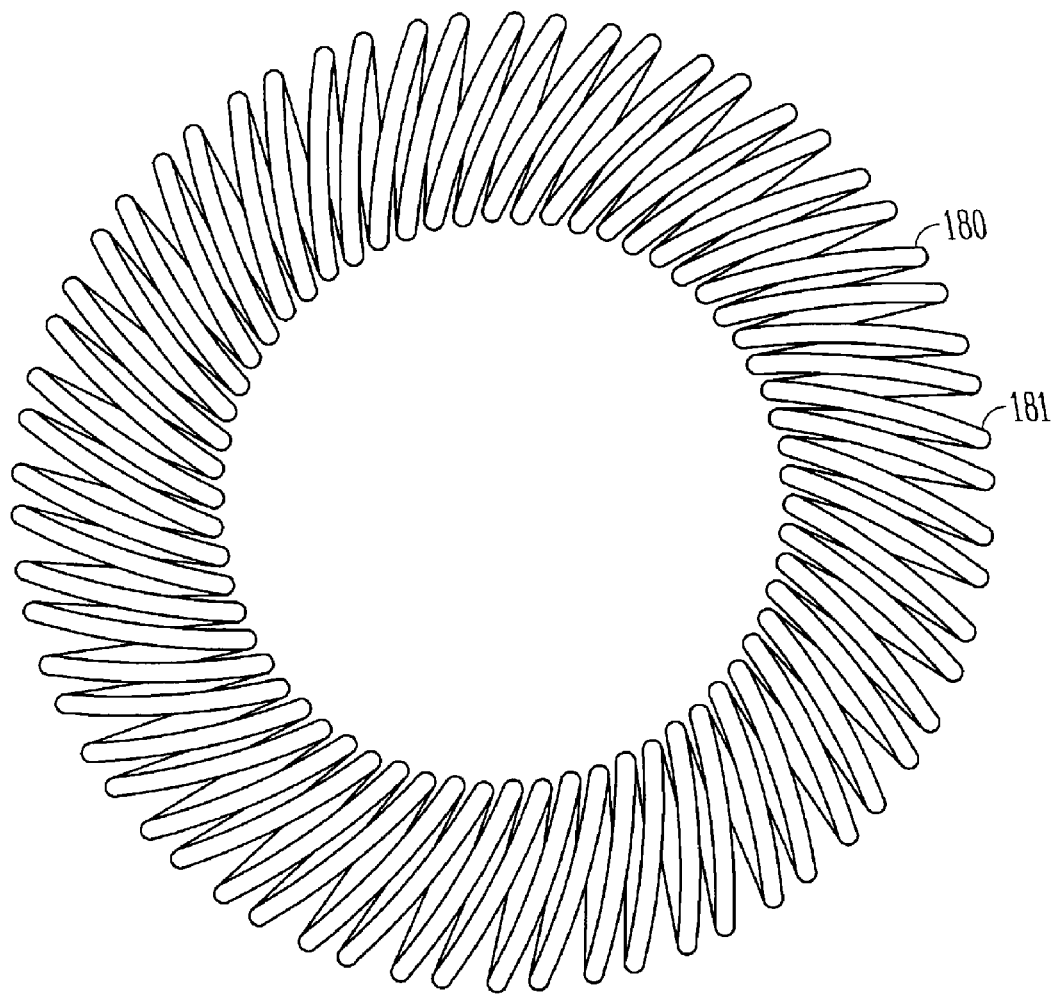
FIG. 5 illustrates a low variation friction member constructed in accordance with at least one embodiment.

Referring again to the friction member 180, an example friction member 180 is a low variation friction member 181, illustrated in greater detail in FIGS. 3A, 3B and 5. In an option, the low variation friction member 181 is retained by a retention member, such as, but not limited to, a recess 182 or a protrusion. In an option, the recess 182 is sized to retain the low variation friction member 181, for example, by interference fit. In another option, the low variation friction member 181 is retained by the piston, for example, the low variation friction member 181 is mechanically coupled with the piston or the active fixation assembly 122 such that the low variation friction member 181 does not move relative to the active fixation assembly 122 as the assembly 122 is moved, either rotationally and/or longitudinally, as shown in FIGS. 7A-10. Further options for retaining the friction member 180 include, but are not limited to, adhesive, welding, or staking.

The low variation friction member 181 provides a substantially linear amount of friction to the distal portion of the lead 110, for example the piston, or the electrode base 160, as the piston is moved to advance the fixation helix 120. For example, as the piston is moved, the amount of frictional force applied to the active fixation assembly does not substantially vary. For example, the amount of frictional force does not vary greater than 25% within the normal working deflection range, where the normal working deflection range is the deflection range experience by the low variation friction member under normal use due to movement and dimensional variation within the tolerance ranges.

Examples of the low variation friction member 180 include any member that provides a frictional force with low variation, for example a non silicone mechanism, or a canted coil. For instance, low variation frictional force includes providing double the deflection with a normal working deflection range resulting in less than double the friction. The normal working deflection range is the deflection range the low variation friction member would experience under normal use due to movement and dimensional variation within the tolerance ranges. In an option doubling the deflection within the normal working deflection range results in no substantial change in friction.

An example low variation friction member 181 is illustrated in FIG. 5, which shows a canted coil. The canted coil provides the ability to design in a specific friction level, and one that isn't dependent on tolerance stack up of the lead assembly. For example, parameters of the canted coil can be modified, or predetermined to deliver a certain amount of friction to the piston. The parameters of the canted coil include, but are not limited to, wire diameter, wire material, cant angle, overall inner diameter, overall outer diameter, or wire wrap diameter.

Figure 6:
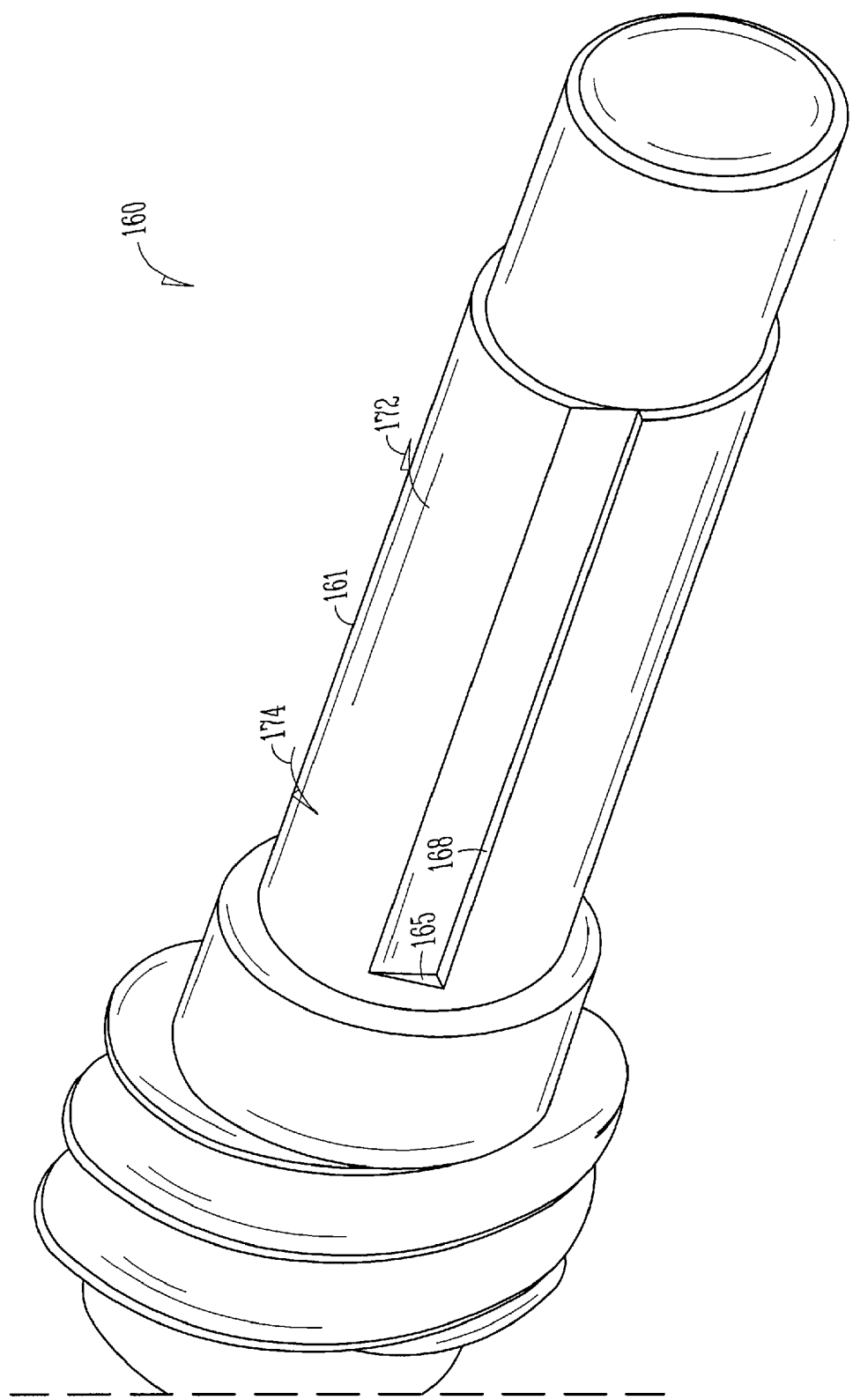
FIG. 6 is a perspective view of an electrode base constructed in accordance with at least one embodiment.
Figure 7A:
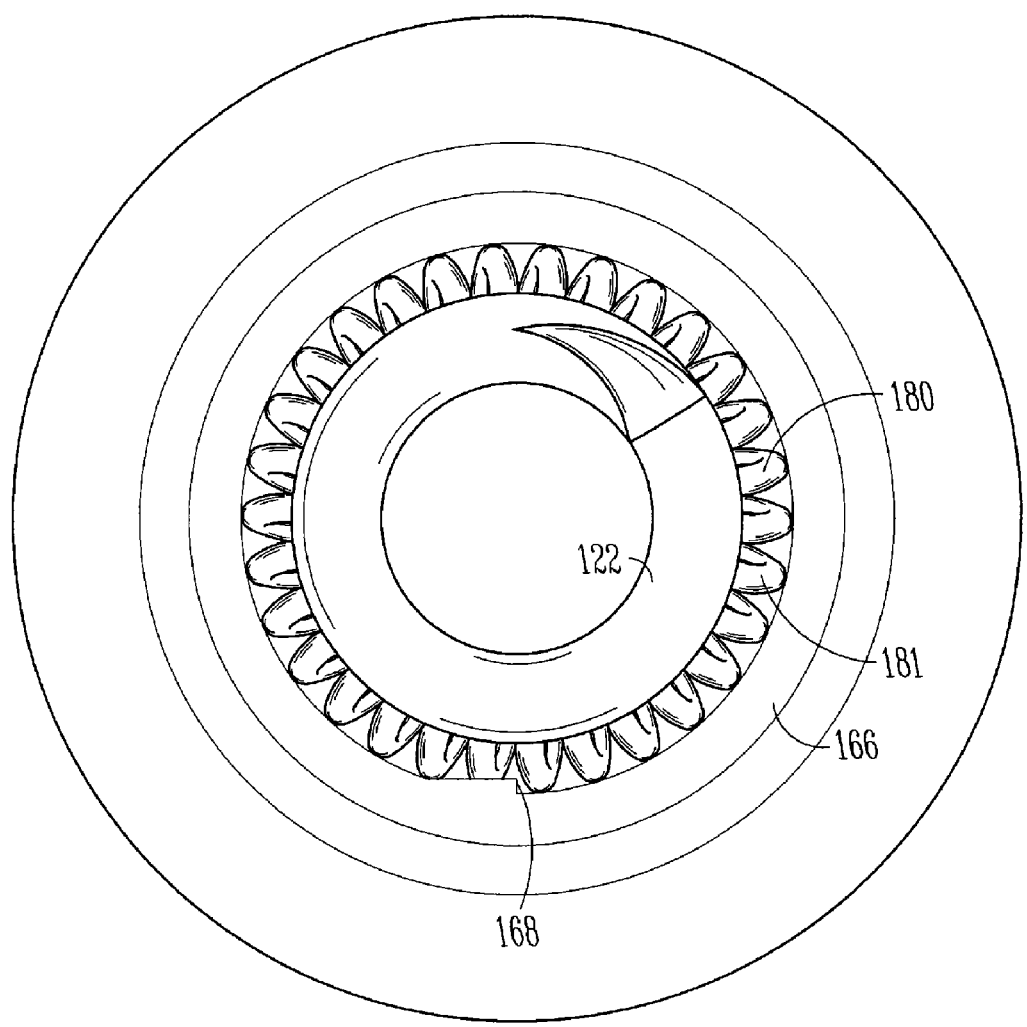
FIG. 7A is an end view of a portion of a lead constructed in accordance with at least one embodiment.
Figure 7B:
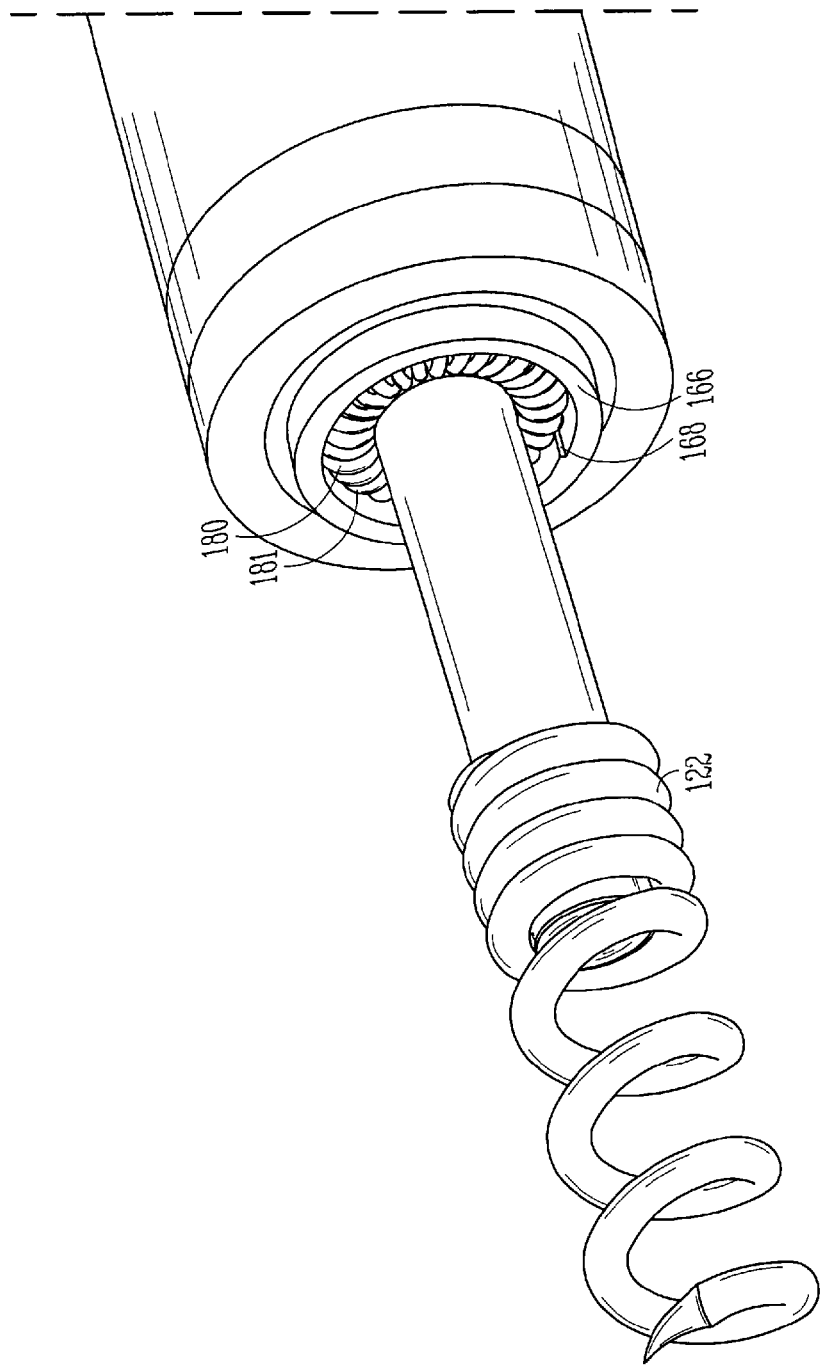
FIG. 7B is a perspective view of a portion of a lead constructed in accordance with at least one embodiment.
Figure 8A:
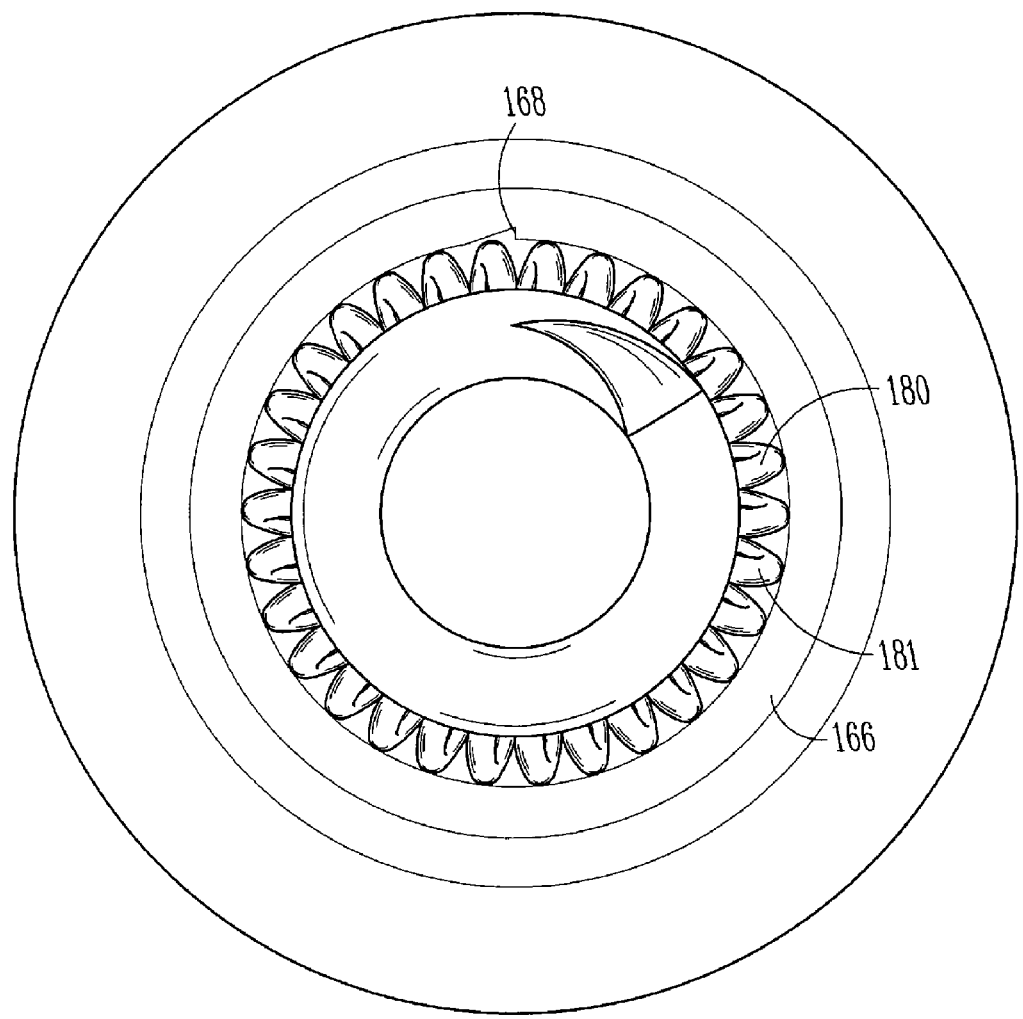
FIG. 8A is an end view of a portion of a lead constructed in accordance with at least one embodiment.
Figure 8B:
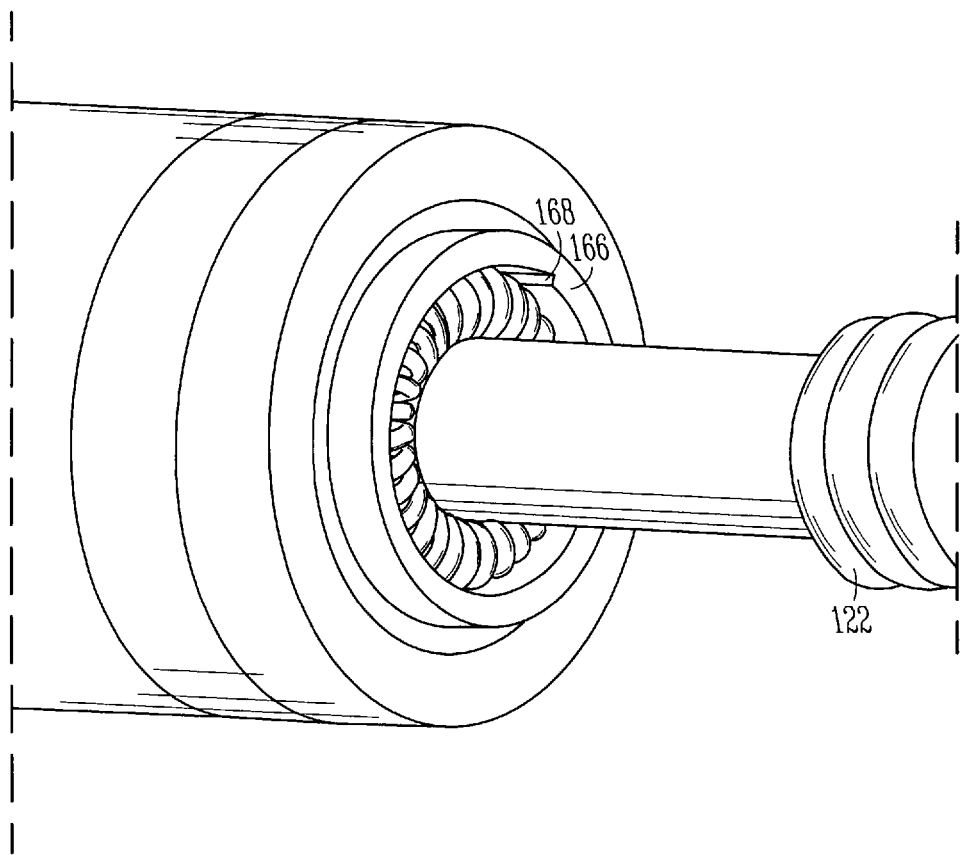
FIG. 8B is a perspective view of a portion of a lead constructed in accordance with at least one embodiment.

FIGS. 6-8 illustrate another example for the electrode base 160 or the piston, which includes a non-circular outer periphery. The electrode base 160 includes a grooved portion in an outer periphery 161 of the electrode base 160. The grooved portion 165 forms a step 168 in the outer periphery 161. The step and the grooved portion 165 interact with the friction member during movement of the electrode base 160. The step 168 is shaped, in an option, that it provides a shelf which, when rotated against the friction member 180 (for example in the direction of 172), must be overcome with a first amount of force. When rotated in the opposite direction (for example in the direction of 174), there is a lesser amount of force necessary to rotate the piston. For example, when rotating the piston and the fixation helix to extend the fixation helix, there is less torsional resistance than when the piston is rotated to retract the fixation helix. For example, greater torsional resistance is applied when the helix is removed from tissue, regardless if the helix and fixation assembly move longitudinally relative to the lead body. The friction member 180, in combination with the non-circular features such as the step of the electrode base, assist in providing resistance to dislodgement of the lead from the patient. Optional grooves 195 (FIG. 10) are provided in the piston, allowing for longitudinal movement of the active fixation assembly 122 as the assembly 122 is rotated.

FIGS. 7A-10 illustrate another example of a step 168 that interacts with the friction member 180. The step 168 is formed either as a projection, shown in FIGS. 7A and 7B, or as a recess, as shown in FIGS. 8A and 8B. When the active fixation assembly 122 is rotated in a first direction, for example a direction to remove the helix with tissue, the friction member 180 interacts with the step 168 and greater torsional resistance is applied. When the active fixation assembly 122 is rotated in the opposite direction, to engage the helix with tissue, lesser torsional resistance is applied because the friction member 180 does not have to overcome the step 168.

A method of using the lead is further described herein. The method includes moving an active fixation assembly of an implantable lead system relative to an elongate, flexible lead body, where the elongate, flexible lead body extends from a proximal portion to a distal portion and the active fixation assembly is within the elongate flexible lead body. The lead system is optionally coupled with an energy source, such as, but not limited to, a pulse generator. The active fixation assembly is moved longitudinally, for example by rotation, to implant the active fixation member in tissue.

The method further includes providing a friction force, such as a linear friction force to the movable active fixation assembly as it is moved relative to the elongate, flexible lead body. An example of providing the linear friction force is placing a canted coil against an outer periphery of the active fixation assembly as the active fixation assembly is moved.

When applying the force, in an option, the method includes placing a first torsional resistance against the active fixation assembly as the active fixation assembly is moved toward an extended position and placing a second torsional resistance against the active fixation assembly. For instance, the second torsional resistance is greater than the first torsional resistance. The extended position includes rotating the active fixation member to implant the active fixation member in tissue without moving the active fixation member longitudinally relative to the lead body. In an option, the method includes riding a friction member against a projection as the active fixation assembly is moved toward a retracted position.

The lead assembly and method therefore described above provides several advantages, for example, a lead that resists dislodgement. For example, the lead retraction components undergo a higher friction during retraction, as compared to extension, thereby reducing the likelihood of mechanism retraction during in vivo use. Furthermore, the lead provides accurate, repeatable, and predictable level of friction within the lead tip, allowing for predictable helix extension, and one which has a low variation of friction over even a relative large component tolerance range.

It is to be understood that the above description is intended to be illustrative, and not restrictive. Although the use of the implantable device has been described for use as a lead in, for example, a cardiac stimulation system, the implantable device could as well be applied to other types of body stimulating systems. Many other embodiments will be apparent to those of skill in the art upon reviewing the above description. The scope should, therefore, be determined with reference to the appended claims, along with the full scope of equivalents to which such claims are entitled.

What is claimed is:

1. A lead system comprising:
   an elongate lead body extending from a proximal end portion to a distal end portion;
   a recess formed in the elongate lead body;
   a low variation friction member held within the recess such that the low variation friction member is held stationary with respect to the elongate lead body, the low variation friction member including an annular spring coil having individual coil windings defining a coil centerline, the coil centerline following an annular path; and
   an active fixation assembly movable relative to the elongate lead body, the active fixation assembly extending through the annular spring coil with the annular path of the centerline encircling the active fixation assembly such that the active fixation assembly can translate relative to the low variation friction member, the low variation friction member being frictionally engaged with the active fixation assembly in order to provide frictional resistance to translation of the active fixation assembly, the active fixation assembly including a piston having a non circular outer periphery that interacts with the low variation friction member.

2. The lead system as recited in claim 1, wherein the low variation friction member is disposed adjacent to a distal tip location of the elongate lead body.

3. The lead system as recited in claim 1, wherein the active fixation assembly includes an electrode base, wherein the low variation friction member is in direct frictional contact with an outer periphery of the electrode base.

4. The lead system as recited in claim 1, wherein the active fixation assembly includes a helix.

5. The lead system as recited in claim 1, wherein the active fixation assembly is movable along a longitudinal axis of the lead body.

6. The lead system as recited in claim 1, wherein the piston includes a step disposed along the outer periphery and the step frictionally engages the low variation friction member when the active fixation assembly is moved in a first direction.

7. The lead system as recited in claim 1, wherein the low variation friction member is stationary relative to the movable active fixation assembly.

8. A method comprising:
   moving an active fixation assembly of an implantable lead system relative to an elongate, flexible lead body, the implantable lead system including an annular spring coil having individual coil windings defining a coil centerline, the coil centerline following an annular path, the annular spring coil held within a recess formed within the elongate flexible lead body such that the active fixation assembly is held stationary with respect to the elongate flexible lead body and the active fixation assembly extends through the annular spring coil, the elongate, flexible lead body extending from a proximal portion to a distal portion; and
   generating a frictional force between the active fixation assembly and the annular spring coil as the activate fixation assembly moves relative to the elongate, flexible lead body;
   wherein generating a frictional force comprises placing a first torsional resistance against the active fixation assembly as the active fixation assembly is moved toward an extended position and placing a second, different, torsional resistance against the active fixation assembly when the active fixation assembly is moved toward a retracted position.

9. The method as recited in claim 8, wherein moving the active fixation assembly includes rotating the active fixation assembly.

10. The method as recited in claim 8, wherein providing the linear friction force to the movable active fixation assembly includes placing a canted coil against an outer periphery of the active fixation assembly as the active fixation assembly is moved.

11. The method as recited in claim 8, further comprising placing a greater torsional resistance on the active fixation assembly as the active fixation assembly is moved toward a retracted position.

12. The method as recited in claim 8, further comprising riding a friction member against a projection as the active fixation assembly is moved toward a retracted position.

13. A lead system comprising:
 an elongate lead body extending from a proximal end portion to a distal end portion;
 at least one conductor disposed within at least a portion of the lead body;
 an active fixation assembly movable relative to the elongate lead body; and
 the active fixation assembly undergoes a first torsional resistance when moved toward an extended position and a second, different, torsional resistance when moved toward a retracted position.

14. The lead system as recited in claim 13, further comprising a friction member interactively coupled with the active fixation assembly.

15. The lead system as recited in claim 14, wherein the friction member is a canted coil disposed around an outer periphery of the active fixation assembly.

16. The lead system as recited in claim 15, wherein the canted coil is disposed adjacent to the distal end portion of the elongate lead body.

17. The lead system as recited in claim 14, wherein the active fixation assembly includes at least one step therealong, and the at least one step interacts with the friction member.

18. The lead system as recited in claim 13, wherein the active fixation member is movable along a longitudinal axis of the lead body.

19. The lead system as recited in claim 13, wherein the second torsional resistance is greater than the first torsional resistance.

20. The lead system as recited in claim 13, further comprising an energy source electrically coupled with the lead system.

21. The lead system as recited in claim 13, further comprising a piston base having at least one step therein, and the at least one step interacts with the friction member.

* * * * *

UNITED STATES PATENT AND TRADEMARK OFFICE
CERTIFICATE OF CORRECTION

Page 1 of 1

| | |
|---|---|
| PATENT NO. | : 8,055,356 B2 |
| APPLICATION NO. | : 11/427167 |
| DATED | : November 8, 2011 |
| INVENTOR(S) | : Eric John Wengreen et al. |

It is certified that error appears in the above-identified patent and that said Letters Patent is hereby corrected as shown below:

Column 6

Line 19:

Add the word -- coil -- before the word "centerline"

Signed and Sealed this
Third Day of January, 2012

David J. Kappos
*Director of the United States Patent and Trademark Office*